(12) United States Patent
Crann, Jr.

(10) Patent No.: US 8,593,627 B2
(45) Date of Patent: Nov. 26, 2013

(54) APPARATUS AND METHOD FOR INSPECTING THE INNER SURFACE OF A TUBULAR STRUCTURE FOR CONTAMINATION

(75) Inventor: William J. Crann, Jr., Bad Axe, MI (US)

(73) Assignee: Millennium Industries Corporation, Ligonier, IN (US)

( * ) Notice: Subject to any disclaimer, the term of this patent is extended or adjusted under 35 U.S.C. 154(b) by 0 days.

(21) Appl. No.: 13/444,418

(22) Filed: Apr. 11, 2012

(65) Prior Publication Data

US 2013/0070240 A1 Mar. 21, 2013

Related U.S. Application Data

(60) Provisional application No. 61/535,036, filed on Sep. 15, 2011.

(51) Int. Cl.
*G01N 21/94* (2006.01)

(52) U.S. Cl.
USPC ...................................... 356/241.1

(58) Field of Classification Search
USPC ............. 356/241.1–241.6, 237.1–237.2, 445; 250/341.1, 341.8
See application file for complete search history.

(56) References Cited

U.S. PATENT DOCUMENTS

| | | | |
|---|---|---|---|
| 2,363,700 A | 11/1944 | Soetbeer | |
| 2,899,856 A | 8/1959 | Shull | |
| 3,551,061 A | 12/1970 | Glowa | |
| 3,761,186 A * | 9/1973 | Wason | 356/241.1 |
| 4,055,382 A * | 10/1977 | Ziekman et al. | 356/446 |
| 4,317,632 A | 3/1982 | Orphan et al. | |
| 4,707,132 A * | 11/1987 | Dutton | 356/600 |
| 4,712,916 A | 12/1987 | Gunn | |
| 4,725,883 A * | 2/1988 | Clark et al. | 348/84 |
| 4,934,813 A | 6/1990 | Yaginuma et al. | |
| 5,004,339 A | 4/1991 | Pryor et al. | |
| 5,317,387 A * | 5/1994 | Van Hengel et al. | 356/625 |
| 5,790,620 A * | 8/1998 | Okazaki et al. | 376/305 |
| 7,505,124 B2 * | 3/2009 | Kreckel et al. | 356/237.1 |
| 7,602,487 B2 | 10/2009 | Fukami et al. | |

(Continued)

OTHER PUBLICATIONS

Wang, Optical Fiber Corrosion Sensor Based on Laser Light Reflection, Smart Materials and Structures 20 (Jun. 28, 2011) 085003 (7pp), IOP Publishing, <http://iopscience.iop.org/0964-1726/20/8/085003>.

(Continued)

*Primary Examiner* — Sang Nguyen
(74) *Attorney, Agent, or Firm* — Dykema Gossett PLLC

(57) ABSTRACT

A method for inspecting the inner surface of a tubular structure for contamination comprises emitting a light beam directed onto the inner surface at a first end thereof, wherein the beam is directed at a predetermined glancing angle such that it repeatedly reflects off of the inner surface of the tubular structure along the length thereof. The method further comprises receiving the reflected beam at a second end of the tubular structure. The method still further comprises measuring a value of the reflectance of the received reflected beam, defining a parameter value using the measured value, and comparing the parameter value with a predetermined threshold value. The method further comprises determining, based on the comparison, the extent to which the inner surface of the tubular structure is contaminated, and displaying an indication representative of the contamination based on the determination. An apparatus for performing the method is also provided.

20 Claims, 3 Drawing Sheets

(56) References Cited

U.S. PATENT DOCUMENTS

| | | | |
|---|---|---|---|
| 7,636,204 | B1 | 12/2009 | Bourget |
| 7,768,660 | B1 | 8/2010 | Pribil et al. |
| 2003/0033880 | A1* | 2/2003 | Lam et al. ............... 73/627 |
| 2009/0235749 | A1* | 9/2009 | Ehara et al. ............. 73/622 |
| 2012/0062728 | A1* | 3/2012 | Oikawa et al. ........ 348/128 |

OTHER PUBLICATIONS

Zhang et al., Non-Contact Laser Inspection for the Inner Wall Surface of a Pipe, Measurement Science & Technology 9 (1998) 1380-1387 <http://iopscience.iop.org/0957-0233/9/9/004>.

Basu et al., Omni-Directional Sensors for Pipe Inspection, Dept. of Computing Science, University of Alberta, Edmonton, Alberta, Canada T6G 2H1, Institute of Electrical and Electronics Engineers International Conference, Oct. 22-25, 1995.

Wu et al., Measurement and Inspection—Non-Contact Inspection for Inner Surface of Small-Diameter Pipes Based on Laser-PSD, Optoelecronics Letters, vol. 1, No. 1 (Jul. 15, 2005), 61-64, DOI: 10.1017/BF03033619.

Keyence, NEO Series General Catalog, Copyright 2011, Keyence Corporation.

* cited by examiner

APPARATUS AND METHOD FOR INSPECTING THE INNER SURFACE OF A TUBULAR STRUCTURE FOR CONTAMINATION

CROSS REFERENCE TO RELATED APPLICATIONS

This application claims the benefit of U.S. Provisional Application Ser. No. 61/535,036 filed on Sep. 15, 2011, which is hereby incorporated by reference in its entirety.

BACKGROUND OF THE INVENTION a. Field of the Invention

The present disclosure is directed to an apparatus and a method for inspecting the inner surface of a tubular structure for contamination. More particularly, the present disclosure is directed to an apparatus and method for inspecting the inner surface of a tubular structure, such as, for example, a fluid conduit for use in fuel delivery systems, for contamination resulting from the manufacture or processing of the tubular structure.

b. Background Art

Fluid delivery systems, such as, for example, vehicular fuel delivery systems, are often comprised of one or more tubularly-shaped fluid conduits each having an inner passageway that allows for the communication of fluid from a source to one or more components downstream from the source. For example, a vehicular fuel delivery system may comprise one or more fluid conduits commonly known as fuel rails that are configured to allow for the communication of fuel from a fuel tank to one or more fuel injectors. These fluid conduits may have any number of cross-sectional shapes, such as, for example and without limitation, circular, square, and rectangular, among others.

In order to avoid the creation of defects in the conduit, care must be taken during the manufacturing process to ensure that the inner surface of the conduit is free, or at least substantially free, from contaminants. For example, the inner surface of the conduit may be contaminated with residue remaining as a result of the processing of the conduit. More particularly, one type of contamination is pilgering oil that has been baked into the inner surface of the conduit. This oil is not easily removed and if the residue is brazed during a brazing operation performed on the conduit, it may create undesirable braze defects in the conduit.

Accordingly, the conduit must be inspected during the manufacturing process to ensure that the inner surface of the conduit is not unacceptably contaminated. One conventional way in which the conduit may be inspected is by visual inspection. Such a technique involves an individual performing a visual inspection from an end of a conduit with or without additional illumination. Another conventional inspection technique involves the use of a boroscope. In such a technique, a boroscope may be inserted into the conduit and may be used to inspect the inner surface thereof. Yet still another conventional technique for inspecting the inner surface of fluid conduits comprises cutting open a sampling of conduits from a given lot of conduits and visually inspecting the cut-down conduits. Based on the visual inspection of those conduits, a determination can be made as to the likelihood that the other conduits in the lot are unacceptably contaminated.

Conventional techniques, such as, for example, those described above, are not without their disadvantages, however. For example, the visual inspection technique where an individual looks down the conduit from one end thereof typically results in only identifying grossly contaminated tubes, or making a determination as to the contamination based on very limited portions of the conduit, namely those portions located proximate each end thereof. This technique is also very subjective and is dependent upon the particular individual inspecting the conduits. Accordingly, if multiple individuals are inspecting the conduits, the inspection and determinations are not necessarily uniform or consistent.

With respect to the use of a boroscope, this approach is very resource intensive. More particularly, this particular technique is time consuming and includes the use of fibers and lenses that wear down over time and, as a result, have to be replaced relatively frequently, which can be relatively expensive. Additionally, and as with the visual inspection technique described above, this technique is also very subjective and is dependent upon the particular individual inspecting the conduits. Accordingly, if multiple individuals are inspecting the conduits, the inspection and determinations are not necessarily uniform or consistent.

With respect to the technique where a sampling of conduits is cut down and inspected, and then the determinations made for those evaluated conduits are applied to other conduits in a common lot, this approach, as with those techniques described above, is relatively expensive, time consuming, and subjective. It is also ineffective unless a relatively large number of conduits are cut down and inspected.

Accordingly, there is a need for a method and system for inspecting the inner surface of tubular structures, such as, for example, fluid conduits (e.g., fuel rails), for contamination that will minimize and/or eliminate one or more of the above-identified deficiencies.

BRIEF SUMMARY OF THE INVENTION

The present invention is generally directed to an apparatus and method for inspecting the inner surface of a tubular structure for contamination.

In accordance with one aspect of the invention, an apparatus for inspecting the inner surface of a tubular structure for contamination is provided. The apparatus comprises an emitter disposed proximate a first end of the tubular structure and configured to emit a light beam directed onto the inner surface thereof at a predetermined glancing angle such that the light beam repeatedly reflects off of the inner surface of the tubular structure along the length thereof. The apparatus further comprises a receiver disposed proximate a second end of the tubular structure opposite the first end, wherein the receiver is configured to receive the reflected light beam. In an exemplary embodiment, the apparatus further comprises an evaluation unit electrically connected to the receiver, as well as an indicator electrically connected to the evaluation unit. In such an embodiment, the evaluation unit is configured to: measure a value of the reflectance of the reflected light beam received by the receiver; define a parameter value using the measured value, compare the parameter value with a predetermined threshold value; determine, based on the comparison, the extent to which the inner surface of the tubular structure is contaminated; and control the indicator to display an indication representative of the contamination of the tubular structure based on the determination. In an exemplary embodiment, the parameter value comprises the actual measured value, while in another exemplary embodiment the parameter value comprises a scaled value corresponding to the measured value and that is based on a predetermined scale.

In another embodiment, the apparatus comprises an emitter disposed proximate a first end of the tubular structure and configured to emit a light beam directed onto the inner surface of the tubular structure at a predetermined glancing angle such that the light beam repeatedly reflects off of the inner surface of the tubular structure along the length thereof. The apparatus further comprises a receiver disposed proximate a second end of the tubular structure opposite the first end, wherein the receiver is configured to receive the reflected light beam. The apparatus further comprises a sensor electrically connected to the receiver and configured to measure a value of the reflectance of the reflected light beam received by the receiver, a control unit electrically connected to the sensor, and an indicator electrically connected to the control unit. In such an embodiment, one of the sensor and the control unit is configured to: define a parameter value using the measured value, compare the parameter value with a predetermined threshold value; and determine, based on the comparison, the extent to which the inner surface of the tubular structure is contaminated. The control unit is further configured to control the indicator to display an indication representative of the contamination of the tubular structure based on the determination. In an exemplary embodiment, the parameter value comprises the actual measured value, while in another exemplary embodiment the parameter value comprises a scaled value corresponding to the measured value and that is based on a predetermined scale.

In accordance with another aspect of the invention, a method for inspecting the inner surface of a tubular structure for contamination is provided. The method comprises the step of emitting a light beam directed onto the inner surface of the tubular structure at a first end thereof, wherein the light beam is directed at a predetermined glancing angle such that the light beam repeatedly reflects off of the inner surface of the tubular structure along the length thereof. The method further comprises the step of receiving the reflected light beam at a second end of the tubular structure opposite the first end thereof. The method still further comprises the steps of measuring a value of the reflectance of the received reflected light beam, defining a parameter value using the measured value, and comparing the parameter value with a predetermined threshold value. The method yet still further comprises the steps of determining, based on the comparison, the extent to which the inner surface of the tubular structure is contaminated, and displaying an indication representative of the contamination of the tubular structure based on the determination. In an exemplary embodiment, the parameter value comprises the actual measured value, and thus, the measuring and creating steps are effectively one in the same, while in another exemplary embodiment the parameter value comprises a scaled value corresponding to the measured value and that is based on a predetermined scale.

Further features and advantages of the present invention, including the constituent components thereof, will become more apparent to those skilled in the art after a review of the invention as it is shown in the accompanying drawings and detailed description.

DETAILED DESCRIPTION OF EMBODIMENTS OF THE INVENTION

Figure 1:
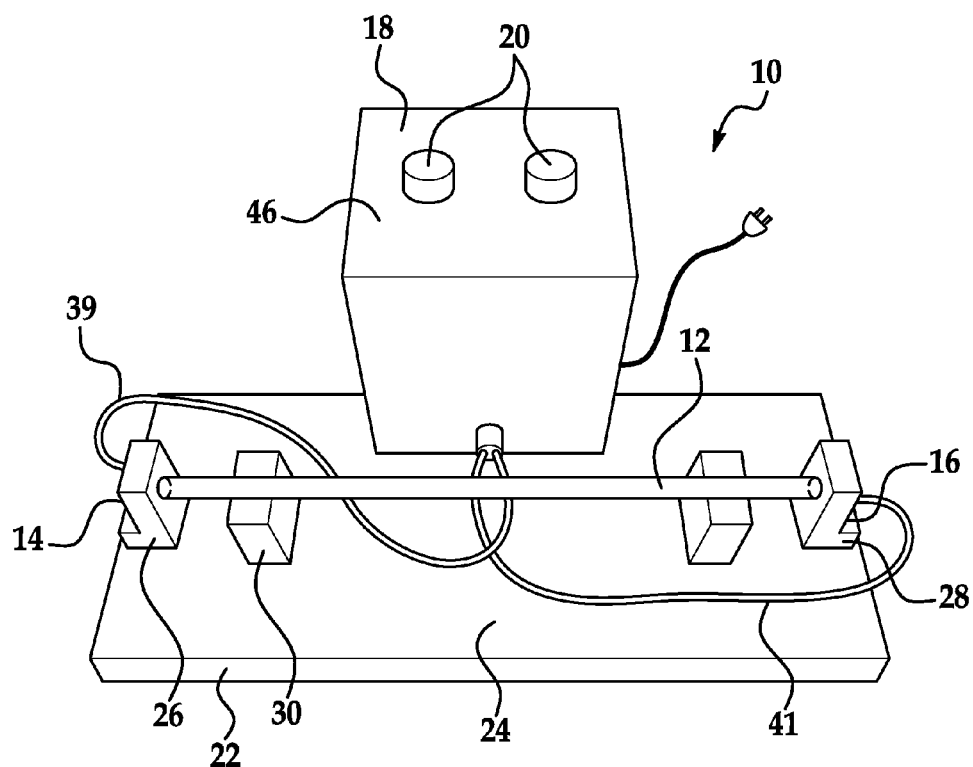
FIG. 1 is a isometric view of an exemplary embodiment of an apparatus for inspecting the inner surface of a tubular structure for contamination.

Referring now to the drawings wherein like reference numerals are used to identify identical components in the various views, FIG. 1 illustrates one exemplary embodiment of an apparatus 10 for inspecting the inner surface of a tubular structure 12 (or tube 12), such as, for example and without limitation, a stainless steel tubular structure, for contamination. In an exemplary embodiment, the apparatus 10 comprises a light source or emitter 14, a light receiver 16, an evaluation unit 18, and an indicator element (or indicator) 20. As will be described in greater detail below, in an exemplary embodiment, both the emitter 14 and the receiver 16 are electrically connected to the evaluation unit 18, and the evaluation unit 18 is, in turn, electrically connected to the indicator 20.

In an exemplary embodiment, the tubular structure 12 comprises a fluid conduit, such as, for example and without limitation, a fuel rail for use in a vehicular fuel delivery system. The tubular structure 12 may have any number of cross-sectional shapes, such as, for example and without limitation, circular, rectangular, square, and the like.

With continued reference to FIG. 1, in an exemplary embodiment, the apparatus 10 further comprises a test stand 22 to which the emitter 14 and the receiver 16 are mounted, and on which the tube 12 is placed when being inspected. Accordingly, in an exemplary embodiment, the test stand 22 comprises a base 24, a first mounting bracket 26 disposed at a first end of the base 24 for mounting the emitter 14 thereto, a second mounting bracket 28 disposed at a second end of the base 24 opposite the first end for mounting the receiver 16 thereto, and one or more tube support members 30 disposed on the base 24 between the first and second mounting brackets 26, 28 and configured to support the tube 12. The test stand 22 is configured to allow the tube 12 to be rotated 360° about the longitudinal axis thereof such that different portions of the inner surface of the tube 12 may be inspected.

Figure 2:
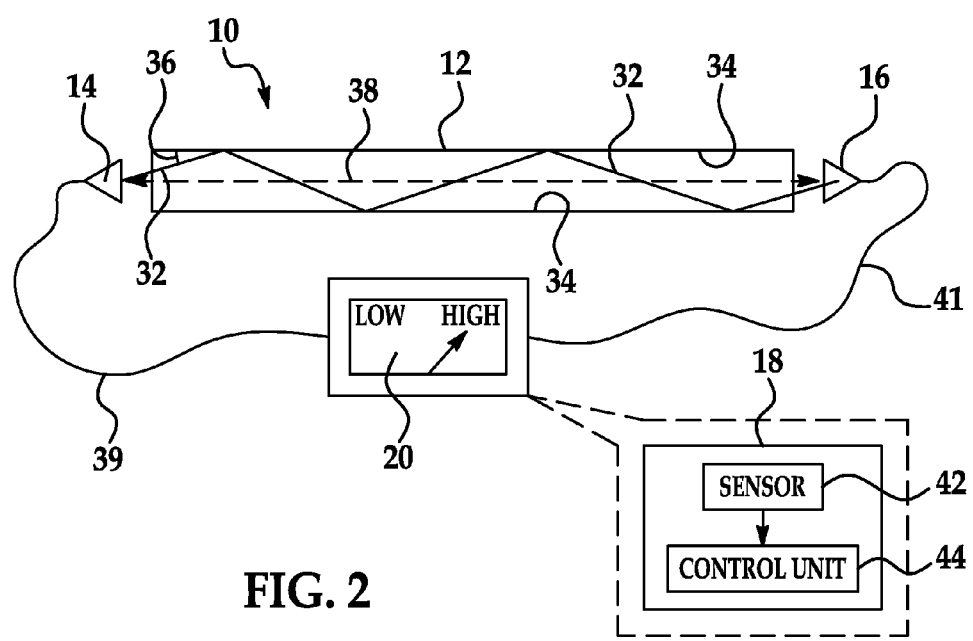
FIG. 2 is a diagrammatic view of another exemplary embodiment of an apparatus for inspecting the inner surface of a tubular structure for contamination.

With reference to FIG. 2, the emitter 14, which is conventional in the art, is configured to emit a beam of light 32 that is ultimately received by the receiver 16. More particularly, the emitter 14 is configured to emit a beam of light 32 directed onto an inner surface 34 of the tube 12 at a first end thereof. Because contaminants on the inner surface 34 of the tube 12 will cause the light beam to scatter and reduce the amount of light reaching a second end of the tube 12, the reflectance or intensity of the light beam received at the second end of the tube can be measured and used to determine the extent to which the inner surface 34 of the tube 12 is contaminated.

Accordingly, and as illustrated in FIG. 2, the light beam 32 emitted or directed in such a manner that it is repeatedly reflected by, or bounced off of, the inner surface 34 of the tube 12 back and forth as the light beam 32 propagates down the length of the tube 12 to a second end where it is received by the receiver 16. The emitter 14 emits the light beam 32 at a predetermined glancing angle 36 relative to the inner surface 34 of the tube 12 that will result in the light beam 32 repeatedly reflecting off of the inner surface 34. In one exemplary embodiment, the angle 36 is eight degrees (8°). It will be appreciated, however, that in other exemplary embodiments, the emitter 14 may be configured to emit the light beam 32 at angles greater or less than that set forth above. Accordingly, the emitter 14 is arranged such that it is pointed sufficiently off-center from the longitudinal axis of the tube 12 (axis 38 in FIG. 2) to achieve the desired angle at which the light is directed onto the inner surface 34 of the tube 12.

In an exemplary embodiment, the emitter 14 comprises a fiber optic unit that emits 640 nm wavelength red light. It will be appreciated, however, that in other exemplary embodiments that remain within the spirit and scope of the present disclosure, emitters or light sources known in the art other than fiber optic units, and/or that emit other colors of light or light having different wavelengths than those set forth above, may be used. In an exemplary embodiment it is preferable that the emitted light be a color other than white so as to avoid interference that may be caused during testing or inspection by ambient light.

In an exemplary embodiment, the emitter 14 may be configured to emit light at different intensities, and as such, the intensity of the light beam 32 emitted by the emitter 14 may vary. The particular intensity of the emitted light beam 32 may depend on a number of factors, such as, for example, the particular components of the apparatus 10, the particular type and/or size (e.g., length and/or diameter) of the tube being inspected, and the particular surface finish of the tube being inspected. In an exemplary embodiment, the intensity level of the emitted light is the highest intensity level possible without saturating components of the evaluation unit 18, such as, for example and as will be described below, a sensor thereof.

In an exemplary embodiment, the emitter 14 is electrically connected to the evaluation unit 18 by one or more electrical cables 39, such as, for example, fiber optic cables, and the evaluation unit 18 may exert a measure of control over the emitter 14. For example, the evaluation unit 18 may dictate the level of intensity of the light beam 32 emitted by the emitter 14. Accordingly, in an exemplary embodiment, the evaluation unit 18, or a particular component thereof, such as the sensor or control unit described more fully below, may include or be electrically coupled to a user interface 40, such as, for example, a button, dial, switch, keypad, keyboard, graphical user interface, or the like, configured to allow a user adjust the intensity of the emitted light beam 32 through the evaluation unit 18.

The receiver 16 is also conventional in the art and is configured to receive the light beam 32 emitted from the emitter 14 after it has been repeatedly reflected by, or bounced off of, the inner surface 34 of the tube 12 along the length thereof. In an exemplary embodiment, the receiver 16 is centered and co-axial with the longitudinal axis 38 of the tube 12. In one embodiment, the receiver 16 is electrically connected to and configured for communication with the evaluation unit 18. In such an embodiment, the receiver 16 may be coupled to the evaluation unit 18 by one or more cables 41, such as, for example, fiber optic cables. In another exemplary embodiment, the receiver 16 is integrated with the evaluation unit 18, and therefore, is a component of the evaluation unit 18 rather than a separate and distinct component of the apparatus 10.

The evaluation unit 18 is configured to, among other things, measure the value of the reflectance or intensity of the reflected light beam 32 received by the receiver 16 and to define a parameter value using the measured value. In an exemplary embodiment, the parameter value comprises the actual measured value, while in another exemplary embodiment it comprises a scaled value of, or corresponding to, the measured value that is based on a predetermined scale (e.g., in an exemplary embodiment, the scaled value will be within the range of, for example, 2000-6000).

In an exemplary embodiment, the evaluation unit 18 is further configured to compare the parameter value with a predetermined threshold value stored in or on a memory or other storage device that is part of or accessible by the evaluation unit 18, and to determine, based on that comparison, the extent to which the tube 12 is contaminated, and more particularly, whether or not the inner surface 34 of the tube 12 is unacceptably contaminated. For example, if the parameter value exceeds (or, in an exemplary embodiment meets or exceeds) the predetermined threshold value, a determination can be made that the inner surface 34 of the tube 12 is free or sufficiently free from contaminants (i.e., the tube is not unacceptably contaminated), while if the parameter value falls below (or, in an exemplary embodiment meets or falls below) the predetermined threshold value, a determination can be made that the inner surface 34 of the tube 12 is unacceptably contaminated.

Figure 3:
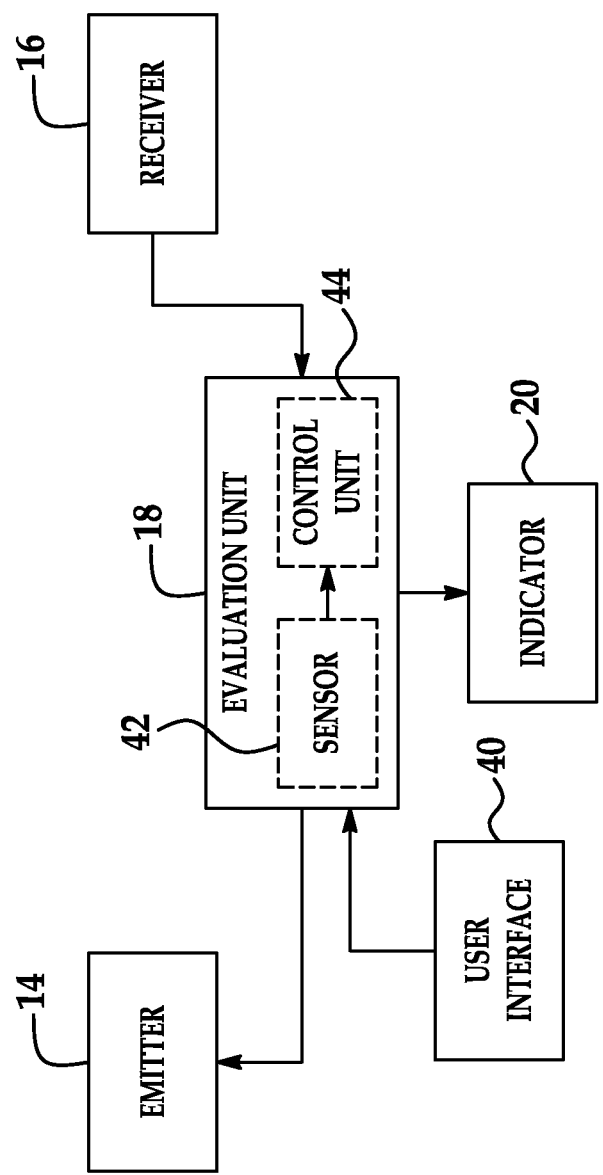
FIG. 3 is a diagrammatic and schematic view of the exemplary apparatuses illustrated in FIGS. 1 and 2.

As illustrated in FIG. 3, in an exemplary embodiment, the evaluation unit 18 comprises a sensor 42 that is configured to perform the measurement, parameter value definition, comparison, and determination functionality described above. The sensor 42 may include a programmable microprocessor or microcontroller, or an application specific integrated circuit (ASIC), that is configured with appropriate programming instructions or code (i.e., software) to perform various functions, such as, for example and without limitation, the comparison function described above and the functionality of the sensor described elsewhere herein. Accordingly, in an exemplary embodiment the sensor 42 is programmed with one or more computer programs encoded on a computer storage medium for performing the functionality of the sensor 42 described herein. As such, the sensor 42 may include or be configured to access a memory or other storage device having one or more predetermined threshold values stored thereon that the sensor 42 may use to determine whether or not the inner surface 34 of the tube 12 is unacceptably contaminated.

In another exemplary embodiment that will be described below, rather than the sensor 42 performing the parameter value definition, comparison, and determination functionality described above, the evaluation unit 18 may comprise a control unit 44 electrically coupled to and configured for communication with the sensor 42 that is configured to perform some or all of this functionality. For example, in such an embodiment, the predetermined threshold value may be stored in or on a memory or other storage device that is part of or accessible by the control unit 44. In an embodiment wherein the control unit 44 is configured to perform some or all of the functionality described above, the sensor 42 may also be part of the evaluation unit 18, or alternatively, may be separate and distinct therefrom, but electrically coupled to and configured for communication with the control unit 44. For instance, the sensor 42 may be integrated with the receiver 16, or may be disposed intermediate both the receiver 16 and the evaluation unit 18.

Regardless of which component of the evaluation unit 18 is configured to perform the parameter value definition, comparison, and determination functions described above, the predetermined threshold value(s) to which the parameter value is compared is dependent upon the intensity of the light beam 32 when it was emitted by the emitter 14, and may also be dependent upon the type and size (e.g., length and diameter) of the tube to be inspected, as well as the surface finish thereof. The threshold value may be empirically determined by bench testing conducted prior to the manufacture of the apparatus 10.

More particularly, in an exemplary embodiment, the threshold value may be determined by testing a tube that from a visual inspection is deemed to have an amount of contamination that is slightly more than an upper limit of what is deemed to be an acceptable amount of contamination, and therefore, the tube is considered to be unacceptably contaminated. In other words, if another tube is at least as contaminated as the tube being tested in the threshold determining process, the tube would be deemed to be unacceptably contaminated. Conversely, if another tube is less contaminated than the tested tube, it would be deemed not to be unacceptably contaminated, and therefore, acceptable.

Accordingly, to determine an appropriate threshold value, a light beam having an intensity and wavelength that is equal to that emitted by the emitter 14 during operation of the apparatus 10 is directed onto the inner surface of the contaminated tube being tested at a first end thereof. The intensity or reflectance of the light beam received at a second end of the tube opposite the first end is measured and recorded. The value is then stored in a memory or other storage device that is part of or accessible by the evaluation unit 18 or one or more components thereof and used as the threshold value corresponding to a light beam having an intensity of that used in the testing process, and thus, of that emitted by the emitter 14. Therefore, in one exemplary embodiment, the threshold value corresponds to the actual values of measured intensity or reflectance. Alternatively, in another exemplary embodiment, the measured intensity or reflectance may be scaled based on a predetermined scale to create a scaled threshold value that may be used. In either instance, the threshold value may be empirically determined based on the limit of the amount of contamination that is deemed to be unacceptable.

In an exemplary embodiment, in order to account for factors or occurrences such as, for example, drift due to power fluctuations of the apparatus 10 and inadvertent movement of cables of the apparatus 10, the threshold value may actually be set to be a certain percentage below that of the threshold value (whether scaled or otherwise) determined in the threshold-determining process described above. For example, in an exemplary embodiment, the threshold value may be set at five percent (5%) below the determined threshold value. For instance, if the scaled threshold value determined during the above-described process is 2200, the threshold value to be used may be set at, for example, 2100.

In another exemplary embodiment, rather than determining the threshold value based on the limit of the contamination that is deemed to be unacceptable as described above, the threshold value may be determined based on the upper limit of the amount of contamination that is deemed to be acceptable. Accordingly, a tube that from a visual inspection is deemed to have an amount of contamination that is at or below the upper limit of what is deemed to be an acceptable amount of contamination, and therefore, is not considered to be unacceptably contaminated, is tested. In such an embodiment, the process described above for setting the threshold value would be carried out in the same manner, and therefore it will not be repeated but rather applies here with equal weight and is incorporated here by reference.

Regardless of how the threshold value is determined, the tolerance or sensitivity of the apparatus 10 may be adjustable. More particularly, in an exemplary embodiment, a number of threshold values may be determined in the exemplary manner described above for a corresponding number of different amounts of contamination. For example, a first threshold value may be determined for no or, at most, a negligible amount of contamination; a second threshold value may be determined for a relatively large amount of contamination; and a third threshold value may be determined for an amount of contamination that is between that corresponding to the first and second threshold values. These different threshold values may be stored in, for example, a table stored in a memory or other storage device that is part of or accessible by the particular component (e.g., the evaluation unit 18 or one or more components thereof) that is configured to make the above-described comparisons. A user of the apparatus 10 may then set or adjust the sensitivity of the apparatus 10 by effectively selecting between the different threshold values. In such an embodiment, the user may make such selections using a user interface, such as, for example, the user interface 40 described above, or a separate and distinct user interface that may comprise for example, a button, dial, switch, keypad, keyboard, graphical user interface, or the like, that is configured to allow a user select or adjust the sensitivity of the apparatus 10.

Further, different threshold values may be determined for different types or sizes of tubes or for tubes having different surface finishes. In such an embodiment, these different threshold values may be stored in, for example, a table stored in a memory or other storage device that is part of or accessible by the particular component (e.g., the evaluation unit 18 or one or more components thereof) that is configured to make the above-described comparisons. The user may adjust the threshold value to be used in the same manner described above for adjusting the sensitivity of the apparatus 10.

Similarly, in an embodiment wherein the emitter 14 may be configured to emit light beams of different intensities, different threshold values may be determined for different intensities. In such an embodiment, these different threshold values may be stored in, for example, a table stored in a memory or other storage device that is part of or accessible by the particular component (e.g., the evaluation unit 18 or one or more components thereof) that is configured to make the above-described comparisons. The user may adjust the threshold value to be used in the same manner described above.

Accordingly, the predetermined threshold value may be a single fixed value that is programmed into the evaluation unit 18 during the manufacture or set up of the apparatus 10, or alternatively, may be adjustable by the user of the apparatus 10.

As briefly described above, in an embodiment wherein the evaluation unit 18 comprises both the sensor 42 and the control unit 44, the sensor 42 is electrically connected to and configured for communication with the control unit 44. In an embodiment wherein the sensor 42 is configured to define the parameter value and/or make the comparison between the parameter value and one or more predetermined threshold values, the sensor 42 is further configured to generate an electrical signal representative of the determination relating to the contamination of the inner surface 34 of the tube 12, and to output the same to the control unit 44. As will be described in greater detail below, the control unit 44 may then use the information represented by the electrical signal in the control of the indicator 20. In an exemplary embodiment, the electrical signal may comprise a digital "high" signal (i.e., a binary "1" signal) when it is determined that the tube is acceptable, and a digital "low" signal (i.e., a binary "0" signal) when it is determined that the tube is unacceptably contaminated. It will be appreciated that the opposite scheme is also applicable whereby a digital "low" may represent that the tube is acceptable and a digital "high" represents that the tube is unacceptably contaminated.

In an exemplary embodiment, the control unit 44 is configured to, among other things and as will be described in greater detail below, control the operation of the indicator 20 in response to the electrical signal(s) received from the sensor 42. As briefly described above, however, in an exemplary embodiment, rather than the sensor 42 defining the parameter value and comparing the parameter value and the predetermined threshold value(s), the control unit 44 is configured to receive an electrical signal generated by the sensor 42 representative of the value of the reflectance or intensity of the reflected light beam 32 measured by the sensor 42, define the parameter value using the measured value (e.g., either the actual measured value or a scaled value corresponding thereto), and compare the parameter value with one or more predetermined threshold values to determine the extent to which the inner surface 34 of the tube 12 is contaminated. For example, if the parameter value exceeds (or, in an exemplary embodiment meets or exceeds) the predetermined threshold value, a determination can be made that the inner surface 34 of the tube 12 is free or sufficiently free from contaminants (i.e., the tube is not unacceptably contaminated), while if the parameter value falls below (or, in an exemplary embodiment meets or falls below) the predetermined threshold value, a determination can be made that the inner surface 34 of the tube 12 is unacceptably contaminated.

The control unit 44 may comprise a programmable microprocessor or microcontroller, or may comprise an application specific integrated circuit (ASIC). The control unit 44 may include a central processing unit (CPU) and an input/output (I/O) interface through which the control unit 44 may receive a plurality of input signals including, for example, electrical signals generated by the sensor 42, and generate a plurality of output signals including, for example, those used to control the indicator 20. The control unit 44 may be configured to perform various functions, such as those described in greater detail elsewhere herein, with appropriate programming instructions or code (i.e., software). Accordingly, the control unit 44 is programmed with one or more computer programs encoded on a computer storage medium for performing the functionality of the control unit 44 described herein.

The indicator 20 is configured to provide or display an indication representative of the extent to which the tube 12 is contaminated. For example, in an exemplary embodiment, the indicator 20 may display an indication as to whether the inner surface 34 of the tube 12 being inspected is unacceptably contaminated. The indicator 20 is responsive to electrical signals provided thereto by, for example, the control unit 44 (or, in an exemplary embodiment and as will be described below, the sensor 42) and may take any number of forms. For example, the indicator 20 may comprise a display device, such as, for example, a computer monitor, configured to display an indication responsive to an electrical signal generated by the control unit 44. The displayed indication may include, for example, a numerical representation of the measured reflectance or intensity value or a scaled value corresponding thereto that may be interpreted by the user of the apparatus 10. Alternatively, another type of indication may be displayed on the screen to indicate to the user of the apparatus 10 whether or not the tube 12 being inspected is unacceptably contaminated.

In another exemplary embodiment, the indicator 20 may comprise one or more lights, the illumination or lack of illumination of which serve to indicate that the tube 12 being inspected is unacceptably contaminated or alternatively free (or sufficiently free) from contamination, or at least not unacceptably contaminated. For example, in the embodiment illustrated in FIG. 1, the indicator 20 comprises a pair of lights, one for indicating that the tube 12 is free (or substantially free) from contamination (i.e., not unacceptably contaminated), and the other for indicating that the tube 12 is unacceptably contaminated. Accordingly, in such an embodiment, depending on whether or not the tube 12 is contaminated, one of the lights is illuminated while the other remains "off."

Other exemplary indicators that may comprise the indicator 20 include, for example, a speaker configured to provide or display an audible indication as to whether or not the tube 12 being tested is unacceptably contaminated, a digital numerical output, a gas gauge type of output (see FIG. 2, for example) having a needle that moves in response to the value of the reflectance or intensity measured by the sensor 42 or a scaled value corresponding thereto, or that points in one direction when the tube 12 is determined to be unacceptably contaminated and in another direction when the tube is free (or sufficiently free) from contamination, or any other indicators known in the art.

If the indicator 20 indicates that the tube 12 is unacceptably contaminated, the user of the apparatus 10 can remove the tube 12 and it may be cleaned or discarded. If, on the other hand, the indicator 20 indicates that the tube 12 is free (or sufficiently free) from contamination (i.e., the tube is not unacceptably contaminated), the tube 12 can be further processed for use in a given application (e.g., in the manufacture of a fluid conduit, such as, for example, a fuel rail for use in a fuel delivery system).

In another exemplary embodiment, the sensor 42 of the evaluation unit 18 is configured to perform all of the functionality described above with respect to the control unit 44. Accordingly, in an exemplary embodiment, the sensor 42 itself may be configured to control the operation of the indicator 20. Therefore, in such an embodiment, the sensor 42 is electrically connected to the indicator 20 and the apparatus 10 may not include a separate control unit, but rather the control unit 44 may be integrated into the sensor 42.

In addition to the above, the apparatus 10 may further comprise a power supply (not shown) that is configured to supply power to some or all of the components of the apparatus 10 (e.g., the emitter 14, the sensor 42, the control unit 44, the indicator 20, etc.). In an exemplary embodiment, the power supply is a conventional 120V AC power supply that may be plugged into a wall outlet. Further, in an exemplary embodiment, the apparatus 10 further comprises a housing or enclosure 46 in which one or more of components of the apparatus 10 may be disposed. For example, the evaluation unit 18 (or one or more components thereof), the power supply, at least a portion of the indicator 20, and the user interface 40 may all be disposed within the housing 46. Alternatively, some or all of the components may be disposed within separate enclosures or housings.

Figure 4:
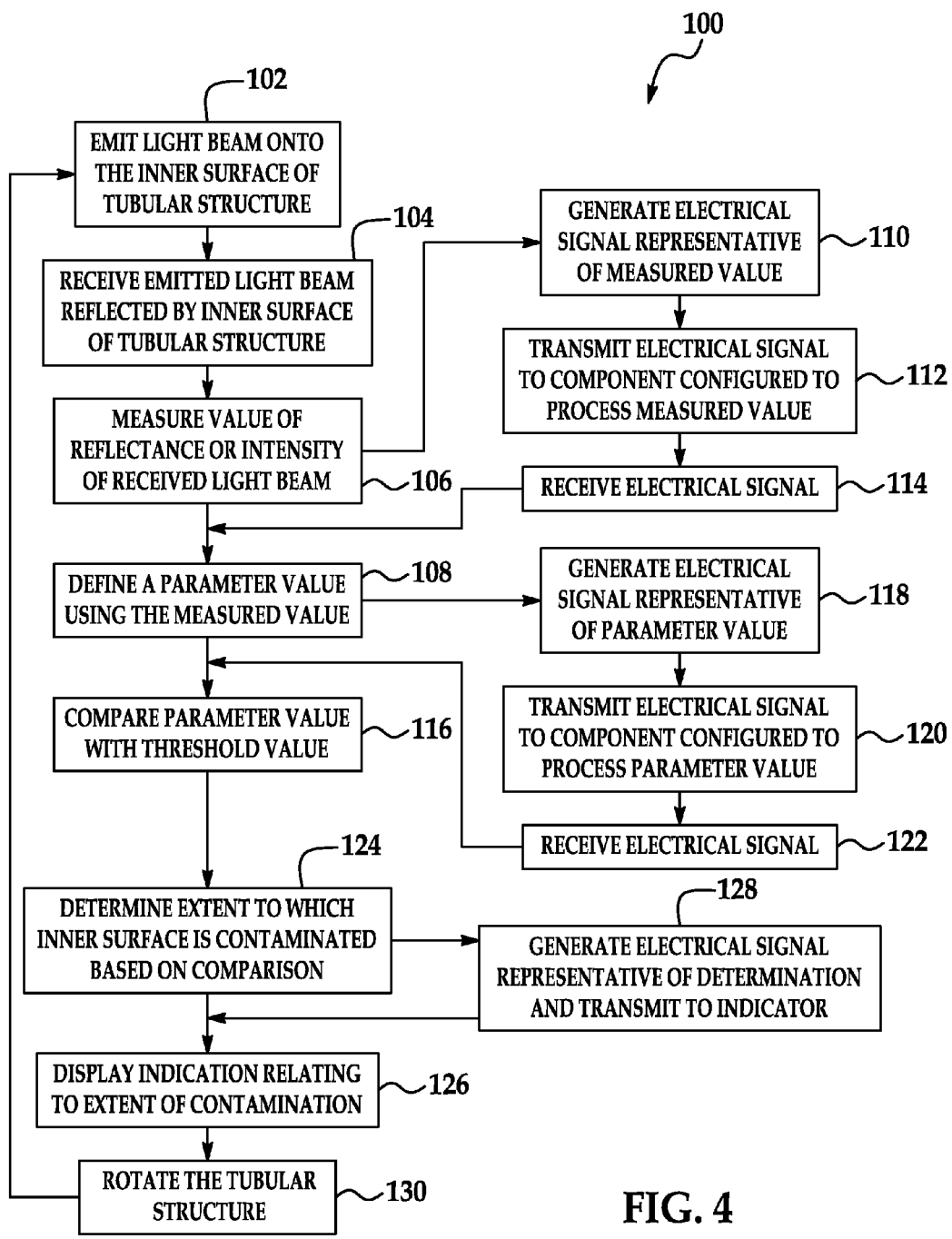
FIG. 4 is a flow chart illustrating an exemplary method for inspecting the inner surface of a tubular structure for contamination.

It will be appreciated that in addition to the structure of apparatus 10 described above, another aspect of the present disclosure is a method 100 for inspecting the inner surface of a tubular structure for contamination. As will be appreciated in view of the description below, one advantage of the method 100 is that it is more objective than conventional techniques, such as, for example, those described elsewhere herein. Accordingly, with respect to FIG. 4, in an exemplary embodiment, the method 100 comprises a first step 102 of emitting a light beam directed onto the inner surface of the tube at a predetermined glancing angle such that the light beam is repeatedly reflected by, or bounced off of, the inner surface of the tube as the light beam travels down the length of the tube. In an exemplary embodiment, the emitting step 102 is performed by an emitter, such as the emitter 14 described above, disposed at a first end of the tube.

The method 100 further comprises a step 104 of receiving the reflected light beam at a second end of the tube opposite the first end. In an exemplary embodiment, the receiving step 104 is performed by a receiver disposed at the second end of the tube, such as, for example, the receiver 16 described above.

The method 100 further comprises a step 106 of measuring the reflectance or intensity of the reflected light beam received by the receiver. In an exemplary embodiment, the measuring step 106 is performed by an evaluation unit, such as, for example, the evaluation unit 18 described above, and more particularly, a sensor thereof, such as, for example, the sensor 42 described above.

In an exemplary embodiment, the method further comprises a step 108 of defining a parameter value using the value measured in step 106. In one embodiment, the parameter value comprises the actual measured value, and therefore, the measuring and defining steps 106, 108 are effectively one in the same. In another exemplary embodiment, however, the parameter value is a scaled value of, or corresponding to, the value measured in the measuring step 106. In such an embodiment, the defining step 108 comprises scaling the measured value in accordance with and based on a predetermine scale. In an exemplary embodiment, the defining step 108 is performed by the evaluation unit 18 described above. More particularly, in one exemplary embodiment, the defining step 108 is performed by the sensor 42 of the evaluation unit 18. However, in another exemplary embodiment, the creating step 108 is performed by a control unit of the evaluation unit 18, such as, for example, the control unit 44 described above, that is electrically connected to and configured for communication with the sensor 42. In such an embodiment, the method 100 further comprises a step 110 of generating, by the sensor, an electrical signal representative of the measured value, a step 112 of outputting or transmitting the generated electrical signal to the control unit, and a step 114 of receiving the electrical signal by the control unit. The control unit uses the information represented by the electrical signal received from the sensor to carry out the defining step 108.

The method 100 further comprises a step 116 of comparing the parameter value with one or more predetermined threshold values. In an exemplary embodiment, the comparing step 116 is also performed by the evaluation unit 18 described above. More particularly, in one exemplary embodiment, the comparing step 116 is performed by the sensor 42 of the evaluation unit 18. However, in another exemplary embodiment, the comparing step 116 is performed by a control unit of the evaluation unit 18, such as, for example, the control unit 44 described above, that is electrically connected to and configured for communication with the sensor 42. In such an embodiment, and wherein the sensor 42 (as opposed to the control unit 44) is configured to perform the defining step 108, the method 100 further comprises a step 118 of generating, by the sensor, an electrical signal representative of the parameter value, a step 120 of outputting or transmitting the generated electrical signal to the control unit, and a step 122 of receiving the electrical signal by the control unit. The control unit uses the information represented by the electrical signal received from the sensor to carry out the comparing step 116.

In an exemplary embodiment, the method 100 still further comprises a step 124 of determining, based on the comparison made in the comparing step 116, the extent to which the tube is contaminated. More specifically, in an exemplary embodiment, the determining step 124 comprises determining whether or not the tube, and the inner surface thereof, in particular, is unacceptably contaminated. In an embodiment wherein the sensor of the evaluation unit performs the comparing step 116, the sensor may also perform the determining step 124. Similarly, in an embodiment wherein the control unit of the evaluation unit performs the comparing step 116, the control unit may also perform the determining step 124.

The method 100 may further comprise a step 126 of providing or displaying an indication in response to the determination made in the determining step 124 representative of the contamination of the tube, or the lack thereof. More particularly, the displaying step 126 may comprise displaying an indication as to whether or not the inner surface of the tube is unacceptably contaminated.

In an exemplary embodiment, the evaluation unit 18, and the sensor 42 or the control unit 44 thereof, in particular, is configured to control an indicator, such as, for example, the indicator 20 described above, to provide or display an appropriate indication as to the contamination of the tube. Accordingly, in one exemplary embodiment wherein the control unit 44 is configured to control the indicator 20, the method 100 comprises a step 128 of generating, by the sensor, an electrical signal representative of the determination relating to the contamination of the tube. The control unit 44 receives the electrical signal from the sensor and then controls the indicator 20 to provide an appropriate indication in response thereto.

Alternatively, In another exemplary embodiment wherein the control unit 44 is configured to determine the extent to which the tube is contaminated, the control unit 44 is configured to make such a determination and then control the indicator to provide an appropriate indication based on that determination.

In yet another in an exemplary embodiment wherein the sensor 42 is configured to control the indicator 20, the sensor 42 determines the extent to which the tube is contaminated, and then controls the indicator 20 to provide an appropriate indication based on that determination.

In an exemplary embodiment, the method 100 further comprises a step 130 of rotating the tube about the longitudinal axis thereof. The tube may be continuously rotated during the course of the inspection process, or may be incrementally rotated in predetermined steps (e.g., repeatedly rotated a particular number of degrees and inspected until the tube has been rotated a total of 360°). As the tube is rotated, the above described methodology is continuously repeated until the tube has been rotated 360° so as to allow for the evaluation of different portions of the inner surface of the tube. If at any time during the testing or inspection of the tube it is determined that a portion of the inner surface is unacceptably contaminated, the entire tube will be deemed to be unacceptably contaminated.

It will be appreciated that additional functionality described in greater detail above with respect to the apparatus 10 may also be part of the inventive methodology. Therefore, to the extent such functionality has not been expressly described with respect to the methodology, the description thereof above is incorporated herein by reference.

Although only certain embodiments have been described above with a certain degree of particularity, those skilled in the art could make numerous alterations to the disclosed embodiments without departing from the scope of this disclosure. Joinder references (e.g., attached, coupled, connected, mounted, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention.

The invention claimed is:

1. An apparatus for inspecting the inner surface of a tubular structure for contamination, comprising:
   an emitter disposed proximate a first end of the tubular structure and configured to emit a light beam directed onto the inner surface of the tubular structure at a predetermined glancing angle such that the light beam repeatedly reflects off of the inner surface of the tubular structure along the length thereof;
   a receiver disposed proximate a second end of the tubular structure opposite said first end, and configured to receive the reflected light beam;
   an evaluation unit electrically connected to said receiver; and
   an indicator electrically connected to said evaluation unit;
   wherein said evaluation unit is configured to:
      measure a value of the reflectance of the reflected light beam received by said receiver;
      define a parameter value using said measured value;
      compare said parameter value with a predetermined threshold value;
      determine, based on said comparison, the extent to which the inner surface of the tubular structure is contaminated; and
      control said indicator to display an indication representative of the contamination of the inner surface of the tubular structure based on said determination.

2. The apparatus of claim 1, wherein said parameter value comprises one of said measured value, and a scaled value of said measured value based on a predetermined scale.

3. The apparatus of claim 1, wherein said evaluation unit is configured to control said indicator to display said indication if the inner surface of the tubular structure is determined to be unacceptably contaminated.

4. The apparatus of claim 1, wherein said evaluation unit comprises a sensor electrically connected to said receiver and configured to:
   measure said value of the reflectance of the reflected light beam received by said receiver;
   define said parameter value using said measured value;
   compare said parameter and predetermined threshold values;
   determine, based on said comparison, the extent to which the inner surface of the tubular structure is contaminated; and
   control said indicator to display said indication.

5. The apparatus of claim 1, wherein said evaluation unit comprises a sensor electrically connected to said receiver, and a control unit electrically connected to said receiver and said indicator.

6. The apparatus of claim 5, wherein:
   said sensor is configured to:
      measure said value of the reflectance of the reflected light beam received by said receiver;
      define said parameter value using said measured value;
      compare said parameter and predetermined threshold values;
      determine, based on said comparison, the extent to which the inner surface of the tubular structure is contaminated; and
      generate an electrical signal representative of said determination and transmit said electrical signal to said control unit; and
   said control unit is configured to:
      receive said electrical signal generated by said sensor; and
      control said indicator to display said indication in response to said electrical signal.

7. The apparatus of claim 5, wherein:
   said sensor is configured to:
      measure said value of the reflectance of the reflected light beam received by said receiver; and
      generate an electrical signal representative of said measured value and transmit said electrical signal to said control unit; and
   said control unit is configured to:
      receive said electrical signal generated by said sensor;
      define said parameter value using said measured value;
      compare said parameter and predetermined threshold values;
      determine, based on said comparison, the extent to which the inner surface of the tubular structure is contaminated; and
      control said indicator to display said indication based on said determination.

8. The apparatus of claim 1, wherein said receiver is integrated with said evaluation unit.

9. The apparatus of claim 1, wherein said emitter is electrically connected to said evaluation unit, and said evaluation unit is configured to exercise a measure of control over said emitter.

10. An apparatus for inspecting the inner surface of a tubular structure for contamination, comprising:
    an emitter disposed proximate a first end of the tubular structure and configured to emit a light beam directed onto the inner surface of the tubular structure at a predetermined glancing angle such that the light beam repeatedly reflects off of the inner surface of the tubular structure along the length thereof;
    a receiver disposed proximate a second end of the tubular structure opposite said first end and configured to receive the reflected light beam;
    a sensor electrically connected to said receiver and configured to measure a value of the reflectance of the reflected light beam received by said receiver;
    a control unit electrically connected to said sensor; and
    an indicator electrically connected to said control unit;
    wherein one of said sensor and said control unit is configured to:
       define a parameter value using said measured value;
       compare said parameter value with a predetermined threshold value; and
       determine, based on said comparison, the extent to which the inner surface of the tubular structure is contaminated; and
    said control unit is configured to control said indicator to display an indication representative of the contamination of the inner surface of the tubular structure based on said determination.

11. The apparatus of claim 10, wherein said parameter value comprises one of said measured value, and a scaled value of said measured value based on a predetermined scale, and said threshold value is a scaled threshold value based on said predetermined scale.

12. The apparatus of claim 10, wherein:
    said sensor is configured to compare said parameter and threshold values and to determine the extent to which the inner surface of the tubular structure is contaminated based on said comparison, said sensor further configured to generate an electrical signal representative of said determination; and said control unit is configured to receive said electrical signal generated by said sensor and to control said indicator to display said indication in response thereto.

13. The apparatus of claim 10, wherein said sensor is configured to generate an electrical signal representative of said measured value, and further wherein said control unit is configured to:

receive said electrical signal generated by said sensor;

define said parameter value using said measured value;

compare said parameter and predetermined threshold values; and determine, based on said comparison, the extent to which the inner surface of the tubular structure is contaminated.

14. The apparatus of claim 10 wherein said control unit is configured to control said indicator to display said indication if the inner surface of the tubular structure is determined to be unacceptably contaminated.

15. The apparatus of claim 10, wherein said sensor is integrated with said receiver.

16. The apparatus of claim 10, wherein said emitter is electrically connected to one of said sensor and said control unit, and said one of said sensor and said control unit is configured to exercise a measure of control said emitter.

17. A method of inspecting the inner surface of a tubular structure, comprising the steps of:

emitting a light beam directed onto the inner surface of the tubular structure at a first end thereof, wherein the light beam is directed at a predetermined glancing angle such that said light beam repeatedly reflects off of the inner surface of the tubular structure along the length thereof;

receiving the reflected light beam at a second end of the tubular structure opposite the first end thereof;

measuring a value of the reflectance of the received reflected light beam;

defining a parameter value using said measured value;

comparing, using an evaluation unit, said parameter value with a predetermined threshold value;

determining, using the evaluation unit, based on said comparison, the extent to which the inner surface of the tubular structure is contaminated; and displaying, using an indicator, an indication representative of the contamination of the inner surface of the tubular structure based on said determination.

18. The method of claim 17, wherein said parameter value comprises one of said measured value, and a scaled value of said measured value based on a predetermined scale.

19. The method of claim 17, wherein said displaying step comprises displaying the indication if the inner surface of the tubular structure is determined to be unacceptably contaminated.

20. The method of claim 17 further comprising the step of generating an electrical signal representative of said determination, and said displaying step comprises displaying said indication in response to said electrical signal.

* * * * *